United States Patent [19]

Tostevin

[11] Patent Number: Plant 6,576

[45] Date of Patent: Jan. 31, 1989

[54] GERANIUM PLANT NAMED YELLOW RIBBONS

[75] Inventor: David Tostevin, Framsden, England

[73] Assignee: White Swan, Ltd., Beaverton, Oreg.

[21] Appl. No.: 585,307

[22] Filed: Mar. 1, 1984

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Kolisch, Hartwell & Dickinson

[57] ABSTRACT

A geranium plant of interspecific origin, characterized by its compact growth habit and primrose-yellow blossoms.

1 Drawing Sheet

1

The present invention relates to a new and distinct variety of geranium plant which was originated by me by crossing a *Pelargonium quinquelobatum* with a *Pelargonium inquinans.*

As the result of this breeding. I have produced a new geranium variety which is endowed with a new and improved combination of characteristics, the most outstanding of which is the true primrose yellow color.

The new geranium variety does not resemble either of its parents, which are salmon and white in flower coloring, nor is it the same as any prior geranium variety. Asexual reproduction of my geranium plant has been performed by me at Ipswich, England and at Farmingdale, N.J., by tissue cultures, but could also be performed by vegetation cutting procedures. Such asexual reproduction has been done for many generations and the unusual and distinctive flower coloring, as well as the other features noted herein, have been fully retained. The new variety is named Yellow Ribbons.

In addition to its distinctive yellow coloring, my new variety exhibits the following features:

(1) good hardiness;

(2) a vigorous, compact habit of growth;

(3) abundant and attractive foliage;

2

(4) all of the blossoms are of the same color;

(5) flowering most of the year indoors and a substantial part of the year outdoors, depending upon the climate;

(6) relatively free flowering with attractive semi-double flowers.

The drawing illustrates the features of my new variety.

More specifically, the flowers are approximately 6 centimeters in diameter when fully open, of semi-double form, and of a true primrose yellow color. The overall color may alternatively be defined by the notation 5.0Y 8/10 according to the Munsell System of Color Notation.

The foliage is plain, non-zoned, smooth texture, medium green, with the underside being slightly more pale than the upper side of the leaf. The foliage generally resembles that of an ivy geranium.

I claim:

1. The new and distinct variety of geranium plant substantially as herein shown and described, characterized particularly as to novelty by the true yellow semi-double flowers, with abundant, compact foliage.

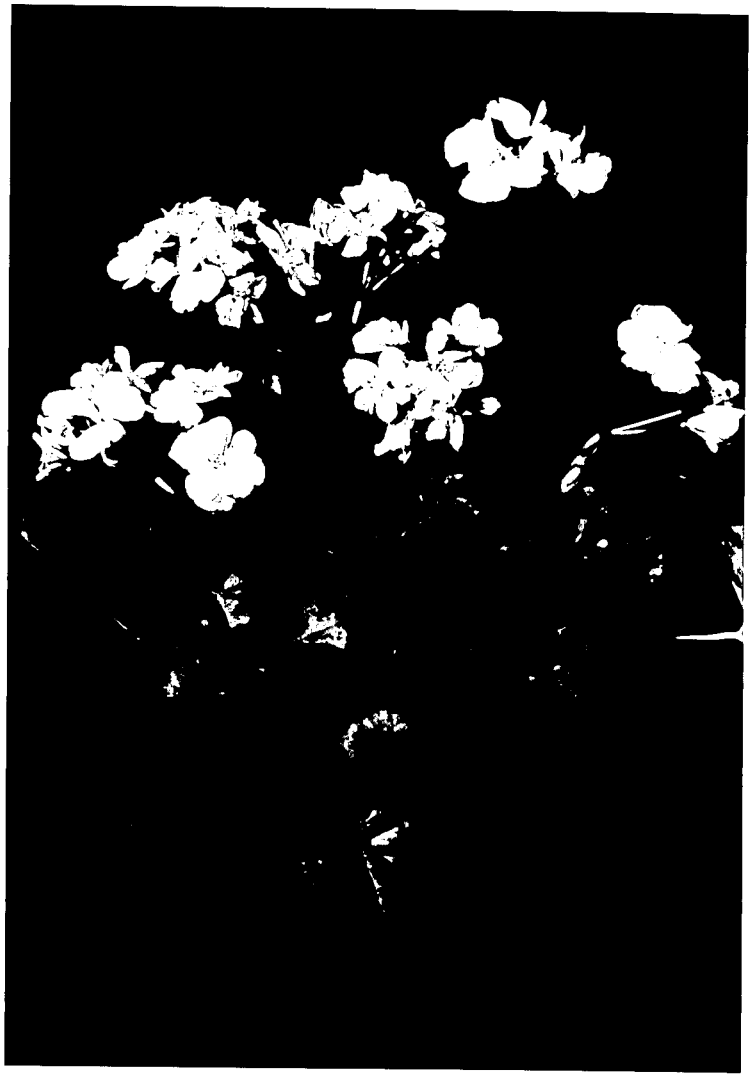

* * * * *